(12) United States Patent
Mihajlovic et al.

(10) Patent No.: US 8,842,953 B2
(45) Date of Patent: Sep. 23, 2014

(54) APPARATUS, METHOD AND COMPUTER PROGRAM FOR APPLYING ENERGY TO AN OBJECT

(75) Inventors: Nenad Mihajlovic, Eindhoven (NL); Szabolcs Deladi, Eindhoven (NL); Joachim Kahlert, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 324 days.

(21) Appl. No.: 12/746,187

(22) PCT Filed: Dec. 2, 2008

(86) PCT No.: PCT/IB2008/055042
§ 371 (c)(1),
(2), (4) Date: Jun. 4, 2010

(87) PCT Pub. No.: WO2009/072060
PCT Pub. Date: Jun. 11, 2009

(65) Prior Publication Data
US 2010/0272398 A1    Oct. 28, 2010

(30) Foreign Application Priority Data
Dec. 6, 2007  (EP) ................................ 07122463

(51) Int. Cl.
*G02B 6/44*  (2006.01)
*G02B 6/06*  (2006.01)
(Continued)

(52) U.S. Cl.
CPC ............ *A61B 18/24* (2013.01); *G02B 6/4416* (2013.01); *A61B 5/6858* (2013.01);

(58) Field of Classification Search
CPC ............ A61B 5/0084; A61B 18/1492; A61B 5/0059; A61B 5/0261
USPC ............ 385/73, 101; 600/29, 342, 372–374, 600/473, 476; 607/15, 16
See application file for complete search history.

(56) References Cited

U.S. PATENT DOCUMENTS

| 4,612,940 A | 9/1986 | Kasevich et al. |
| 5,057,106 A | 10/1991 | Kasevich et al. |

(Continued)

FOREIGN PATENT DOCUMENTS

| EP | 1044654 A2 | 10/2000 |
| GB | 2356464 A | 5/2001 |
| WO | 9639963 A1 | 12/1996 |

OTHER PUBLICATIONS

Arruda et al: "A Novel Mesh Electrode Catheter for Mapping and Radiofrequency Delivery at the Left Atrium-Pilmonary Vein Junction: A Single-Catheter Approach to Pulmonary Vein Antrum Isolation"; Journal of Cardiovascular Electrophysiology, Feb. 2007, vol. 18, No. 2, pp. 206-211.

(Continued)

*Primary Examiner* — Ryan Lepisto
*Assistant Examiner* — Robert Tavlykaev

(57) ABSTRACT

An apparatus for applying energy to an object and/or sensing the object. The apparatus includes an optical device for applying and/or sensing light energy and an electrical device for applying and/or sensing electrical energy. At least one optical fiber is provided for applying light energy to the object and/or sensing the object. The at least one optical fiber is connected to the optical device and includes a conductive coating forming an electrical conductor for applying electrical energy to the object and/or sensing the object. The electrical conductor is connected to the electrical device.

19 Claims, 5 Drawing Sheets

(51) Int. Cl.
*A61B 5/00* (2006.01)
*A61B 5/04* (2006.01)
*A61B 6/00* (2006.01)
*A61N 1/00* (2006.01)
*A61B 18/14* (2006.01)
*A61B 18/24* (2006.01)
*A61B 18/22* (2006.01)
*A61B 17/00* (2006.01)
*A61B 5/042* (2006.01)
*A61B 18/00* (2006.01)
*A61B 18/18* (2006.01)

(52) U.S. Cl.
CPC ...... *A61B 2018/2216* (2013.01); *A61B 5/0084* (2013.01); *A61B 18/1492* (2013.01); *A61B 2017/00026* (2013.01); *A61B 5/042* (2013.01); *A61B 5/6885* (2013.01); *A61B 2018/00214* (2013.01); *A61B 2018/00077* (2013.01); *A61B 2018/2244* (2013.01); *A61B 18/1815* (2013.01); *A61B 2018/00148* (2013.01); *A61B 5/6886* (2013.01); *A61B 2017/00867* (2013.01); *A61B 2017/00057* (2013.01); *A61B 2017/003* (2013.01); *A61B 2017/00022* (2013.01)
USPC .......... 385/101; 385/117; 600/342; 600/373; 600/476; 607/15

(56) References Cited

U.S. PATENT DOCUMENTS

| | | | |
|---|---|---|---|
| 5,415,653 A * | 5/1995 | Wardle et al. | 606/7 |
| 5,546,413 A | 8/1996 | Lebby et al. | |
| 5,628,313 A * | 5/1997 | Webster, Jr. | 600/374 |
| 5,647,867 A | 7/1997 | Neuberger et al. | |
| 5,836,946 A | 11/1998 | Diaz et al. | |
| 6,016,440 A | 1/2000 | Simon et al. | |
| 6,304,784 B1 | 10/2001 | Allee et al. | |
| 6,592,580 B1 | 7/2003 | Stockert | |
| 7,149,391 B1 | 12/2006 | El-Sherif | |
| 2004/0181139 A1 | 9/2004 | Falwell et al. | |
| 2005/0107706 A1* | 5/2005 | Zuluaga et al. | 600/473 |
| 2005/0119647 A1* | 6/2005 | He et al. | 606/41 |
| 2006/0013543 A1* | 1/2006 | Walt et al. | 385/101 |
| 2007/0049833 A1 | 3/2007 | Tearney et al. | |

OTHER PUBLICATIONS

Nakagawa et al: "Development of Micro-Wiring on the Outer Wall of a Catheter"; Sixth International Symposium on Micro Machine and Human Science, Oct. 1995, pp. 137-143.

* cited by examiner

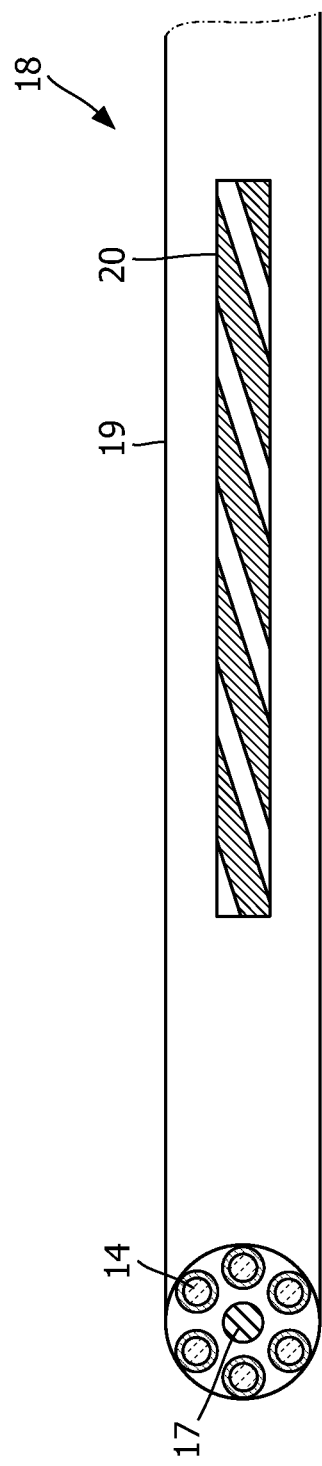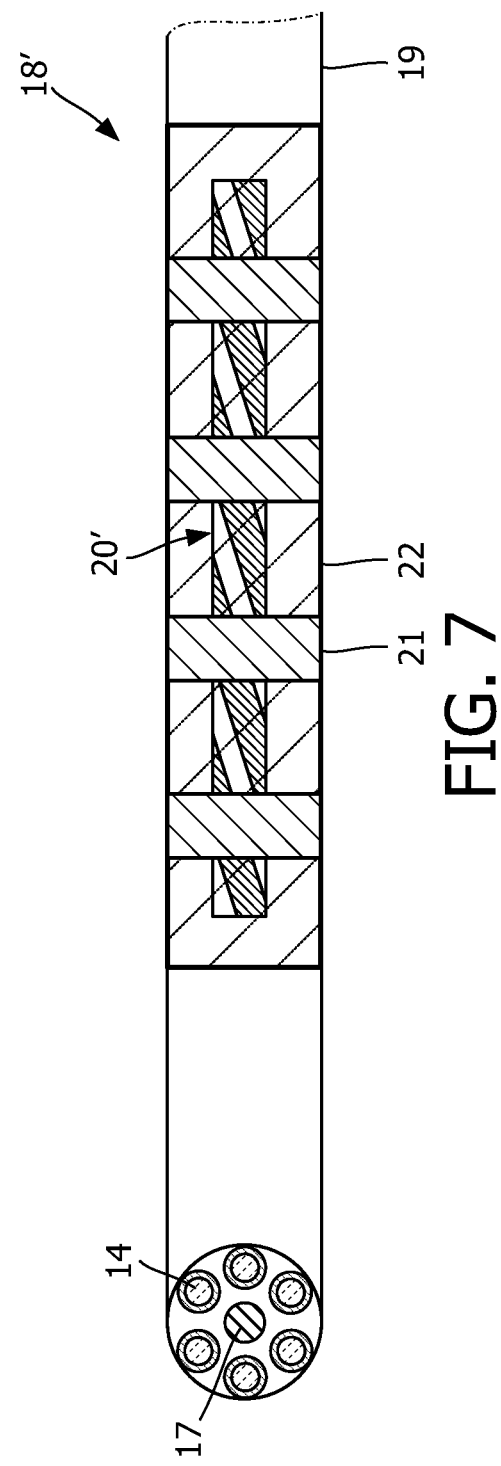

APPARATUS, METHOD AND COMPUTER PROGRAM FOR APPLYING ENERGY TO AN OBJECT

CROSS REFERENCE TO RELATED APPLICATIONS

Related applications are PCT/IB2008/054984 (Apparatus, Method and Computer Program for Applying Energy to an Object) filed Nov. 27, 2008 and IB2008/054965 (Apparatus, Method and Computer Program for Applying Energy to an Object) filed Nov. 26, 2008, which are entering the U.S. national stage concurrently with this application.

FIELD OF THE INVENTION

The invention relates to an apparatus, a method and a computer program for applying energy to an object and/or sensing the object. The invention relates further to a combination element for use in the apparatus for applying energy to an object and sensing the object and a method for producing the apparatus.

BACKGROUND OF THE INVENTION

Apparatuses for applying energy to an object and sensing the object are, for example, used in the field of interventional treatment of atrial fibrillation. During the interventional procedure cardiac tissue is denaturalized by thermal therapy. Radio Frequency energy is applied to the cardiac tissue by a catheter, wherein due to resistive losses in the tissue the myocardium is heated up. The heated muscle cells in the cardiac tissue die off and lose their biological function, which can be measured by an increase in the tissue impedance.

US 2004/0181139 A1 discloses an apparatus for applying energy to an object and sensing the object. This apparatus is a system with a catheter for electrical sensing and electrical ablation within a human heart. The catheter comprises several wires for electrical ablation and for electrical sensing. Since the catheter provides a limited space, the number of wires located within the catheter is limited, wherein the number of ablation points, to which energy can be applied simultaneously and which can be electrically sensed, is limited.

SUMMARY OF THE INVENTION

It is an object of the present invention to provide an apparatus, a method and a computer program for applying energy to an object and/or sensing the object, wherein the degree of integration of energy application elements and sensing elements is increased. It is a further object of the present invention to provide a corresponding combination element for use in the apparatus for applying energy to an object and sensing the object and a method for producing the apparatus.

In an aspect of the present invention an apparatus for applying energy to an object and/or sensing the object is presented, wherein the apparatus comprises:

an optical device for applying and/or sensing light energy,
an electrical device for applying and/or sensing electrical energy,
at least one optical fiber for applying light energy to the object and/or sensing the object, wherein the at least one optical fiber is connected to the optical device, wherein the at least one optical fiber comprises a conductive coating forming an electrical conductor for applying electrical energy to the object and/or sensing the object, wherein the electrical conductor is connected to the electrical device.

The invention is based on the idea that for applying electrical energy to the object and/or for electrical sensing of the object a conductive coating on optical fibers is used, which are already present for applying and/or sensing light energy. Thus, additional wires are not required, wherein the space needed for electrical application elements and electrical sensing elements is reduced and wherein the degree of integration is increased. Furthermore, since an application of light energy and an electrical sensing or an application of electrical energy and an optical sensing, i.e. a sensing of light energy, do not interfere, energy application and sensing can be performed concurrently.

The apparatus preferentially comprises a tube, in particular a catheter, in which the optical fibers are located for guiding the optical fibers to the location, at which energy has to be applied, i.e., if the apparatus is used for, for example, an ablation procedure within a heart chamber, the optical fibers with the conductive coating are located within a catheter for guiding the light energy to the human heart.

The apparatus preferentially further comprises guiding means for steering and/or navigating the tube containing the at least one optical fiber with the conductive coating to the location, at which the energy has to be applied, in particular within an inner space of an object, like a heart chamber.

The optical fiber is preferentially adapted for a laser ablation procedure applied to tissue of the object and the conductive coating is preferentially adapted for electrically sensing the tissue.

In a preferred embodiment the apparatus comprises a multiple of optical fibers comprising a conductive coating forming an electrical conductor, wherein the optical fibers and the electrical conductors formed by the conductive coating are individually addressable. This allows applying energy to different locations of the object and to sense the properties of the object at different locations, in particular simultaneously. Thus, the delivery of energy can be controlled by sensing the properties of the object, like the electrical potential, at the different locations. Preferentially, the apparatus further comprises a control unit for controlling the energy delivery at the different locations in dependence on the sensed property at the different locations, preferentially such that the sensed property at the different locations does not exceed a predetermined threshold.

It is preferred that the conductive coating is coated with an electrically insulating coating. Thus, the optical fibers can be arranged close together, without having a distance between them. This further increases the degree of integration and reduces the space needed for the optical fibers with the conductive coating within a tube like a catheter.

It is further preferred that the apparatus comprises a combination element comprising a multiple of the optical fibers with the conductive coating, wherein the optical fibers with the metal coating are wound around a holding element. The combination element combines the multiple of optical fibers. Since the optical fibers with the conductive coating are wound around the holding element, the optical fibers with the conductive coating are arranged close together in a longitudinal direction with respect to the holding element, i.e. with respect to the helix formed by the wound optical fibers, leading to a reduced distance between locations, at which energy can be applied, in particular simultaneously.

The apparatus comprises preferentially a multiple of combination elements.

The holding element is preferentially a wire. It is also preferred that the holding element has a memory-shape effect such that it has a predetermined shape, if it is not in a forced shape, for example, because the holding element is inside a tube, which keeps the holding element in a certain shape, for example, in a linear shape. This allows guiding the optical fibers with the conductive coating to the locations, at which energy is to be applied, while the combination elements are in a linear shape within the tube, wherein the holding element can give the combination elements a predetermined shape for the application of energy, after the combination element has left the tube at the locations, at which energy is to be applied. The holding element is preferentially a memory metal alloy wire, in particular a nitinol wire. The predetermined shape of the combination element is preferentially a curved shape.

Several combination elements can constitute an arrangement having a predetermined shape outside the tube and being in a forced shape, in particular, in a linear shape, if they are located inside the tube. This arrangement can, for example, have a predetermined shape, which corresponds to an umbrella or basket structure.

It is also preferred that a multiple of combination elements form an arrangement, in particular a basket or umbrella structure, which is changeable between a folded condition, in which the multiple of combination elements are parallel to each other, and an unfolded condition, in which the multiple of combination elements are not parallel to each other, in particular, in which they need more space than in the folded condition and in which the optical fibers with the conductive coating are located on a surface of a volume, in particular an elliptical or spherical volume, defined by the combination elements. This allows guiding the combination elements to the locations, at which energy is to be applied, within a tube, while the combination elements are in the folded condition, wherein, after the locations, at which energy is to be applied, have been reached, the combination elements can leave the tube and can be transformed into the unfolded condition. Preferentially, in the unfolded condition the combination elements are in contact with a surface of the object for applying energy and sensing the object.

In a preferred embodiment the combination element comprises a casing, in which the multiple of optical fibers with the conductive coating and the holding element are located. The casing separates the inside of the casing, in particular the optical fibers with the conductive coating, from the outside of casing, which is, for example, a heart chamber, in which blood is present. The casing is preferentially elastic such that the combination element can be shaped according to the shape of the holding element, in particular if the holding element has a memory effect. The casing is preferentially made of a biocompatible material. It is further preferred that the casing is adapted such that optical and electrical energy can be exchanged between the inside and the outside of the casing, i.e. that the casing is at least partly optically transparent and electrically conductive.

It is further preferred that the casing comprises a window, which is at least partly optically transparent and at least partly electrically conductive, wherein at least a part of the conductive coating is removed at a location, at which the window is optically transparent. This allows transmitting light between the inside and the outside of the casing. If the optical fibers comprise a cladding and possible further coatings, also this cladding and the possible further coatings are removed at these locations. Preferentially micro-lenses for focusing and/or steering light can be added to the window. It is further preferred that the window comprises spreading particles that preferentially do not absorb light, like $TiO_2$. The electrically conductive window or the electrically conductive part of the window is preferentially electrically in contact with the conductive coating of the optical fibers, which should receive or apply an electrical signal. This contact is preferentially located at a place, at which an electrical signal should be received or applied.

The window preferentially comprises an optically transparent part and an electrically conductive part, wherein the optically transparent part is not electrically conductive. This inhibits a transmission of an electrical signal from the object through the optically transparent part of the window, which could be the heart. It is further preferred that the window is dimensioned in the longitudinal direction such that each optical fibers with the conductive coating is optically and electrically accessible. The window preferentially comprises at least two kinds of material, an optically transparent material and an electrically conductive material, wherein the optically transparent material is located at locations, at which light energy should be transmitted, and wherein the electrically conductive material is located at locations, at which the electrical energy should be transmitted. If the conductive coating is covered with an electrically insulating coating, this electrically insulating coating is removed at a location, at which electrical sensing should be performed, i.e. at a location at the electrically conductive window, at which electrical signals should be received by the conductive coating on the optical fibers. The electrically conductive window comprises preferentially titanium or platinum-iridium. The window is preferentially biocompatible.

It is further preferred that at least a part of the window is formed by a tube-shaped or ring-shaped material arranged around the casing and at a position, at which an opening is located in the casing. This facilitates the manufacturing process of the combination element, because firstly the combination element with the casing has to be produced. Then, an opening can be made at a desired location with a desired size, and, after that, the tube-shaped or ring-shaped material can be arranged around the casing. The decision about the size and position of the window can be made in a late step within the manufacturing process. The material is preferentially at least partly optically transparent and/or electrically conductive. Furthermore, the material comprises preferentially fixing elements for fixing the material at the desired position. The material can, for example, have elastic properties or can, for example, be glued to the casing.

The window preferentially comprises alternately optically transparent and electrically conductive parts. This allows applying optical or electrical energy at a location and sensing a property of the object electrically or optically very close to the location, at which the energy is applied. This improves the quality of monitoring a property of the object during the application of energy.

In a further aspect of the present invention a combination element for use in the apparatus as defined in claim 1 is presented, wherein the combination element comprises a multiple of the optical fibers with a conductive coating, wherein the optical fibers with the metal coating are wound around a holding element.

In a further aspect of the present invention a method for applying energy to an object and sensing the object is presented, wherein the method comprises following steps:

applying and/or sensing light energy using at least one optical fiber, which is connected to an optical device, applying and/or sensing electrical energy using a conductive coating on the at least one optical fiber forming an electrical conductor, wherein the electrical conductor is connected to the electrical device.

In a further aspect of the present invention a method for producing an apparatus for applying energy to an object and sensing the object as defined in claim 1 is presented, wherein the method comprises following steps:

providing an optical device for applying and/or sensing light energy, an electrical device for applying and/or sensing electrical energy and at least one optical fiber for applying light energy to the object and/or sensing the object, forming at least one electrical conductor for applying electrical energy to the object and/or sensing the object by coating the at least one optical fiber with a conductive coating, connecting the at least one optical fiber with the optical device, and connecting the at least one electrical conductor with the electrical device.

In a further aspect of the invention a computer program for applying energy to an object and sensing the object is presented, wherein the computer program comprises program code means for causing a computer to carry out the steps of the method as defined in claim 11, when the computer program is run on a computer controlling an apparatus as defined in claim 1.

It shall be understood that the apparatus of claim 1, the combination element of claim 10, the method of claim 11 and the computer program of claim 13 have similar and/or identical preferred embodiments, in particular as defined in the dependent claims.

It shall be understood that preferred embodiments of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following FIGS. 4 and 7 show schematically and exemplarily embodiments of a combination element.

DETAILED DESCRIPTION OF EMBODIMENTS

Figure 1:
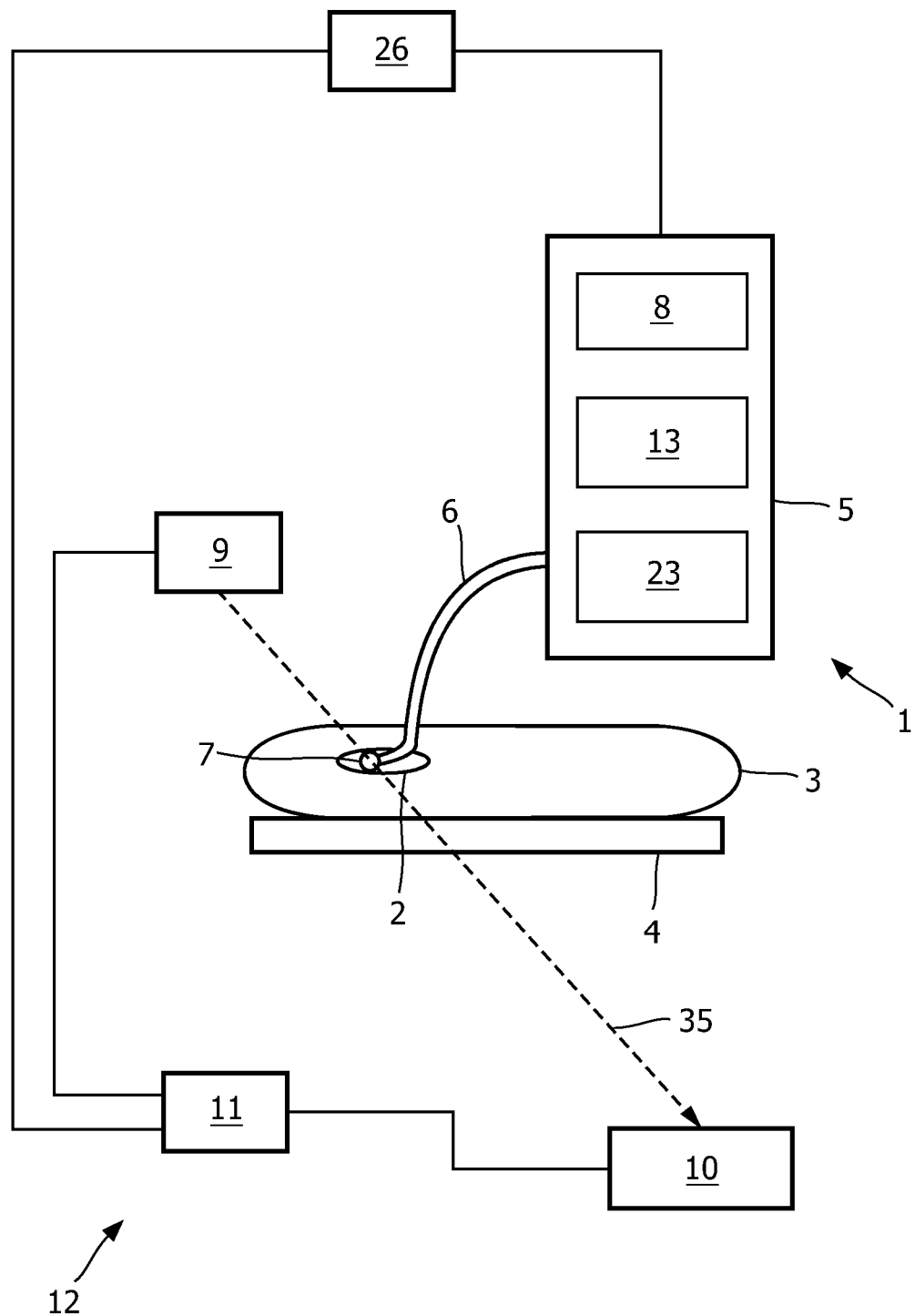
FIG. 1 shows schematically and exemplarily an embodiment of an apparatus for applying energy to an object and sensing the object in accordance with the invention.

FIG. 1 shows an apparatus 1 for applying energy to an object and/or sensing the object. The apparatus 1 comprises a tube, in this embodiment a catheter 6, and an arrangement 7 of energy emitting elements and sensing elements. The arrangement 7 of energy emitting elements and sensing elements is connected to a first control unit 5 via the catheter 6. The catheter 6 with the arrangement 7 of energy emitting elements and sensing elements can be introduced into an object 2, which is, in this embodiment, a heart of a patient 3 located on a patient table 4, wherein the catheter 6 is steered and navigated to the heart chamber by build-in guiding means (not shown) which can be controlled from outside by the guiding control unit 23. In another embodiment, the catheter can, for example, be steered and navigated by the use of guide wires to guide the catheter passively into the heart. Also the guide wires can be controlled by the guiding control unit 23.

During introduction of the arrangement 7 and the catheter 6 into the object 2 an imaging device 12, which is in this embodiment a fluoroscopy device, generates images of the object 2 and the arrangement 7. This imaging device 12 preferentially generates images of the object 2 and the arrangement 7, also if the arrangement 7 is already located within the object 2.

In other embodiments, the object can, for example, be another hollow organ of a patient or a technical object, in particular a hollow technical object, whose inner surface has to be treated with energy.

The imaging device 12, i.e. in this embodiment, the fluoroscopy device 12, comprises an X-ray source 2 and a detection unit 10, which are controlled by a fluoroscopy control unit 11. The imaging device 12 generates X-ray projection images of the object 2 and of the arrangement 7 in a known way. The X-rays of the X-ray source 9 are schematically indicated by the arrow 35.

In another embodiment instead of a fluoroscopy device, another imaging device can be used for generating an image comprising the object 2 and the arrangement 7. For example, a magnetic resonance imaging device, an ultrasonic imaging device or a computed tomography device can be used for generating an image of the object 2 and the arrangement 7.

The first control unit 5 comprises the guiding control unit 23, an optical device 8 for applying and/or sensing light energy and an electrical device 13 for applying and/or sensing electrical energy. The catheter 6 comprises at least one optical fiber for applying light energy to the object and/or sensing the object, wherein the at least one optical fibers is connected to the optical device 8.

Figure 2:
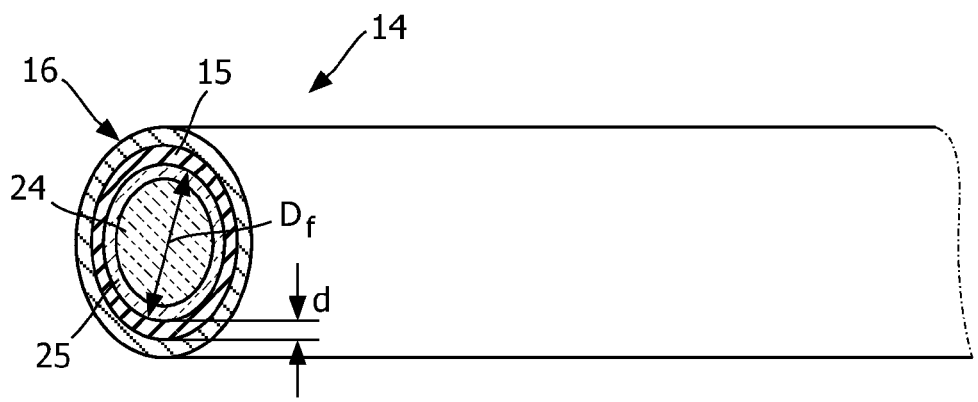
FIG. 2 shows schematically and exemplarily an optical fiber comprising several coatings.

The at least one optical fiber is schematically and exemplarily shown in FIG. 2.

The optical fiber 14 shown in FIG. 2 comprises a fiber core 24, which is surrounded by a cladding 25. The cladding 25 is coated within an electrically conductive coating 15 and the electrically conductive coating 15 is coated with an electrically insulating material 16. The electrically conductive coating 15 comprises, preferentially, titanium, silver or gold, and the electrically insulating material 16 is preferentially a plastic or glass material, in particular, parylene, further preferred parylene-C.

The electrically conductive coating 15 forms an electrical conductor for applying electrical energy to the object and/or sensing the object, wherein the electrical conductor is connected to the electrical device 13.

The apparatus comprises, in this embodiment, a multiple of the optical fibers 14, wherein the optical fibers 14 and the electrical conductors formed by the conductive coating 15 are individually addressable. For example, the optical device 8 comprises several laser devices, wherein each laser device is connected to a single optical fiber, in order to address the optical fibers individually. In another embodiment, beam splitters, shutters and other elements for switching light can be used for addressing different optical fibers individually. The electrical device 13 is adapted such that it is connected to each electrical conductor formed by the conductive coating 15 separately, in order to address each of these electrical conductors independently. For addressing each electrical conductor individually, the electrical device comprises a dedicated circuit and/or a multiple of sources of electrical energy, like radio frequency sources. If the electrical conductors are used for an electrical sensing, for example, for sensing the electrical potential of the object, the electrical device 13 is adapted such that at least some of the electrical conductors can be used for sensing different locations of the object simultaneously and independently from each other, i.e. the electrical device comprises a corresponding circuit and/or a plurality of electrical detection devices for detecting electrical signals received by the electrical conductors.

This allows applying energy to different locations of the object and to sense the properties of the object at different locations, in particular simultaneously. Thus, the application of energy can be controlled by sensing the properties of the object, like the electrical potential, at the different locations. The apparatus 1 further comprises a second control unit 26 for controlling the application of energy at the different locations in dependence on the sensed property at the different locations, preferentially such that the sensed property at the different locations does not exceed a predetermined threshold. The second control unit 26 is preferentially further adapted for controlling the imaging device 12.

Figure 3:
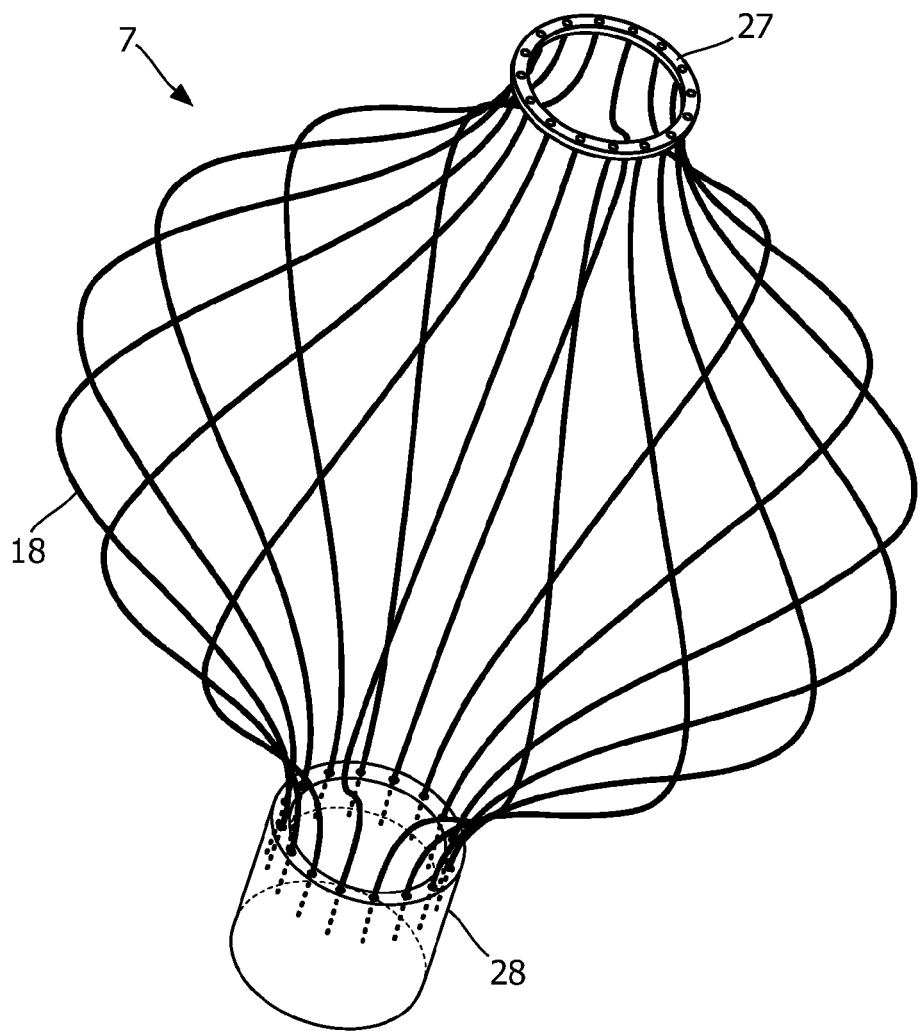
FIG. 3 shows schematically and exemplarily an arrangement of combination elements in an unfolded condition.

FIG. 3 shows schematically and exemplarily the arrangement 7 of energy emitting elements and sensing elements. The arrangement 7 comprises several combination elements 18, which will in the following be explained with reference to FIG. 4.

Each combination element 18 comprises a multiple of optical fibers 14 with the conductive coating 15, wherein the optical fibers 14 with the conductive coating 15 are wound around a holding element 17. The holding element is, in this embodiment, a wire having a memory-shape effect such that is has a predetermined shape, if it is not in a forced-shape, for example, because the holding element 17 is inside the catheter 6, which keeps the holding element 17 in a certain shape, for example, in a linear shape. The holding element 17 is in this embodiment a nitinol wire.

The combination element 18 comprises a casing 19, in which the multiple of optical fibers 14 with the conductive coating 15 and the holding element 17 are located. The casing 19 is preferentially generated by coating the bundle of optical fibers 14 surrounding the holding element 17. The casing 19 separates the inside of the casing 19, in particular the optical fibers 14 with the conductive coating 15, from the outside of the casing 19, which is, for example, a heart chamber, in which blood is present. The casing 19 is elastic such that the combination element 18 can be shaped according to the shape of the holding element 17, in particular, if the holding element 17 has memory effect. The casing 19 is preferentially made of a biocompatible material. The casing 19 is preferentially made of polytetrafluoroethylene (PTFE), high-density-polyethelene (HDPE) and/or polyetherblockamide (PEBA).

The casing 19 comprises a window 20, which is at least partly optically transparent and at least partly electrically conductive, wherein at least a part of the conductive coating 15 is removed at a location, at which the window 20 is optically transparent, in order to allow light, which is guided within the fiber core 24, leaving the fiber core 24 and transmitting through the window 20 for applying light energy to the object. Since, in this embodiment, the optical fiber comprises not only the conductive coating 15, but also the cladding 25 and an electrically insulating material 16, also these materials are removed from the fiber core 24 at a location, at which light should leave the fiber core 24 and transmit through the window 20.

Figure 5:
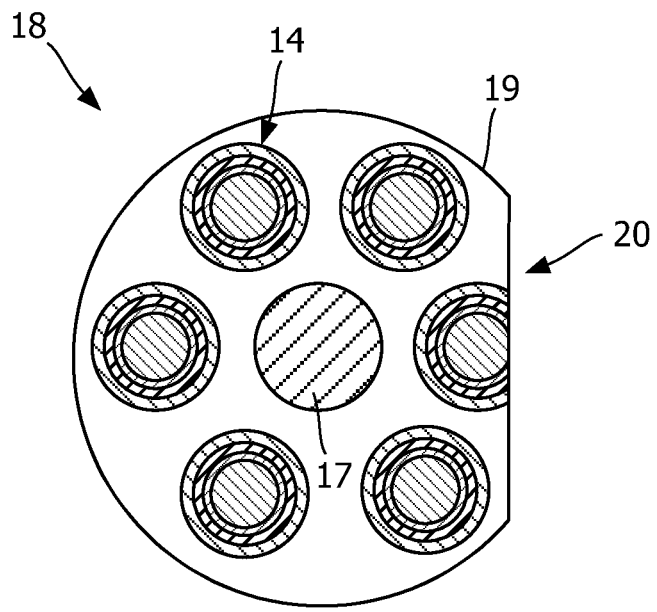
FIGS. 5 and 6 show schematically and exemplarily sectional views through a combination element.

FIG. 5 shows schematically and exemplarily a sectional view through the combination element 18, wherein at the window 20 at a location, at which light should leave the fiber core 24 and transmit through the window 20, the cladding 25, the electrically insulating material 16 and the conductive coating 15 have been removed, in particular, by grinding.

The window 20 preferentially comprises micro-lenses for focusing and/or steering light. It is also preferred that the window 20 comprises spreading particles that preferentially do not absorb light, like $TiO_2$.

At locations, at which electrical signals should be received by the electrical conductor formed by the conductive coating 15 from the object through the window 20, the insulating material 16 is removed from the conductive coating 15, in order to allow the conductive coating 15 to receive electrical signals, which are transferred via the electrical conductor to the electrical device 13. The electrically conductive window 20 or the electrically conductive part of the window 20 is preferentially electrically in contact with the conductive coating 15 of the optical fibers 14, at locations, at which electrical signals should be received.

Figure 6:
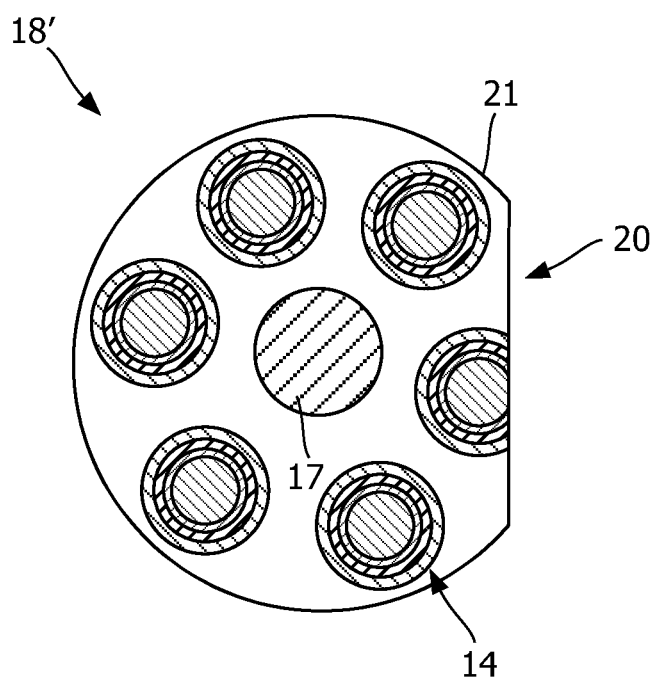

FIG. 6 shows schematically and exemplarily a sectional view through a combination element 18', wherein at the window 20 at a location, at which electrical signals should be received, the insulating material 16 has been removed. The window 20 comprises at this location an electrically conductive ring 21, which should be in contact with the surface of the object during sensing and which is in contact with the conductive coating 15 for transmitting electrical signals from the surface of the object via the conductive coating 15 to the electrical device.

In FIGS. 6 and 7 the conductive ring 21, which could also be a conductive coating, at the opening is preferentially in contact with the conductive coating of one optical fiber 14.

In this embodiment, the window 20 comprises an optically transparent part and an electrically conductive part, wherein the optically transparent part is not electrically conductive. The window 20 is dimensioned in the longitudinal direction such and the optically transparent parts and the electrically conductive parts are arranged such that each fiber core 24 of the optical fibers 14 and each electrical conductor formed by the conductive coating 15 of the optical fibers 14 is optically and electrically accessible, respectively. The electrically conductive part comprises preferentially titanium or platinum-iridium. The window 20 is biocompatible. The optically transparent part of the window 20 is preferentially made of plastic or glass material, preferentially of parylene, further preferred of parylene-C. Preferentially, also the tube, in particular, the catheter, and each element of the apparatus 1, which could be placed in a human body, is biocompatible.

The optical fiber shown in FIG. 2 and the combination elements shown in FIGS. 4 and 7 are shown such that the left side of the optical fiber and the combination elements is open. The left open side is only shown for illustrating the arrangement of elements within the optical fiber and within the combination elements, but, in real, the left sides shown in FIGS. 2, 4 and 7 are closed such that preferentially all light energy is reflected, and is also coated with an electrical insulating material. The right hand side shown in FIGS. 4 and 7 is preferentially connected, in particular, plugged in, to the optical device and the electrical device.

The casing, which is, for example, shown in FIGS. 4 and 7 can be a coating. Furthermore, the optical fibers can be directly wound around the holding element, preferentially if they comprise an outer insulating coating or if they are not electrically conductive, or with a distance to the holding element. In the latter case, spacers can be arranged in between or the casing can comprise lumen, which are generally separated from each other and in which the optical fibers are located, and which are in connection, where required for forming energy emission and/or sensing locations.

Referring again to FIG. 3, the multiple of combination elements 18 form the arrangement 7, which is changeable between a folded condition, in which the multiple of combination elements 18 are parallel to each other, and an unfolded condition, which is shown in FIG. 3 and in which the multiple of combination elements 18 are not parallel to each other and in which the windows 20 of the combination elements 18 are preferentially located on a surface of a volume, in particular, of an elliptical or spherical volume, defined by the combination elements 18. This allows guiding the combination elements 18 to the locations, at which energy is to be applied, within the catheter 6, while the combination elements 18 are in the folded condition, wherein, after the locations, at which energy is to be applied, have been reached, the combination elements 18 can leave the catheter 6 and can be transformed into the unfolded condition shown in FIG. 3. The catheter 6 and the arrangement 7 are, in this embodiment, guided such at least some of the windows 20 of the combination elements 18 are in contact with a surface of the object for applying energy and sensing the object.

One end of the combination elements 18 is attached to a ring element 27 and the other end of the combination elements 18 is attached to a shaft 28.

The combination elements 18 are fixed together at the shaft 28. Preferentially, the combination elements 18 are bundled together by gluing. Furthermore, the combination elements 18 are fixed at the distal end using the ring element 27. In another embodiment, another element can be used for fixing the combination elements 18 at the distal end, for example, a cap could be used.

A further embodiment of a combination element is schematically and exemplarily shown in FIG. 7, wherein similar elements in FIGS. 4 and 7 have similar reference signs.

In FIGS. 4 and 7 only the fiber core and the conductive coating of the optical fibers is shown. But, preferentially each optical fiber shown in FIGS. 4 and 7 comprises the different coatings shown in FIG. 2.

FIG. 7 shows a combination element 18' comprising a casing 19, in which a window 20' is formed by making an opening in the casing 19 and by covering the opening by ring-shaped materials 21, 22. The ring-shaped materials 21, 22 surround the casing 19, wherein the ring-shaped material 21 is electrically conductive and the ring-shaped material 22 is optically transparent. At a location, at which the electrically conductive material is arranged, the insulating material 16 of at least one optical fiber 14 is removed for allowing receiving of electrical signals and at locations, at which the optically transparent material 22 is located, the insulating material 16, the conductive coating 15 and the cladding 25 are removed from the fiber core 24, in order to allow light leaving the fiber core 24 through the optically transparent material 22.

The locations of the optical fibers 14, at which the insulating material 16 is removed, and the electrically conductive material of the window, in particular, the ring-shaped materials 21, are arranged such that there is no short-circuit between the electrically conductive material of two or more fibers, i.e. an electrically conductive region of the window, which is electrically in contact with the electrically conductive material of an optical fiber, is separated by an electrically non-conductive region from another electrically conductive region of the window, which is electrically in contact with the electrically conductive material of another optical fiber. In particular, each of the ring-shaped materials 21 is in contact with only one optical fiber, i.e. with the electrically conductive material of only one optical fiber.

For electrically sensing a surface of the object the electrically conductive material 21 of the window 20' is in contact with the surface of the object and also the electrical conductor formed by the conductive coating 15 of the optical fiber 14 is in contact with the electrically conductive material 21 of the window 20', in order to transmit electrical signals from the surface of the object, in particular from heart tissue, via the electrically conductive material 21 and the conductive coating 15 of a single fiber to the electrical device 13 for measuring the electrical signal and, in particular, the electrical potential. For example, electrical signals which occur in the left atrium of a heart can be measured.

A preferred thickness of the conductive coating 15 is given by following equation:

$$d = -\frac{D_f}{2} + \sqrt{\frac{D_f^2}{4} + \frac{\rho l}{R\pi}}.$$

In the above mentioned equation R denotes a needed resistance of the coating, $D_f$ denotes the diameter of the combination of the fiber core 24 and the cladding 25, l denotes the length of the coated optical fiber inside the catheter, $\rho$ denotes the specific electrical resistance of the material of the conductive coating 15 and d the thickness of the conductive coating 15.

If, for example, the conductive coating 15 is a copper coating ($\rho=1.7\times10^{-8}$ $\Omega$m) with a diameter $D_f=100\times10^{-6}$ m and with a length of l=1.2 m, which can achieve a resistance of R=150$\Omega$, the thickness of the conductive coating 15 is about $d=4\times10^{-9}$ m.

Figure 8:
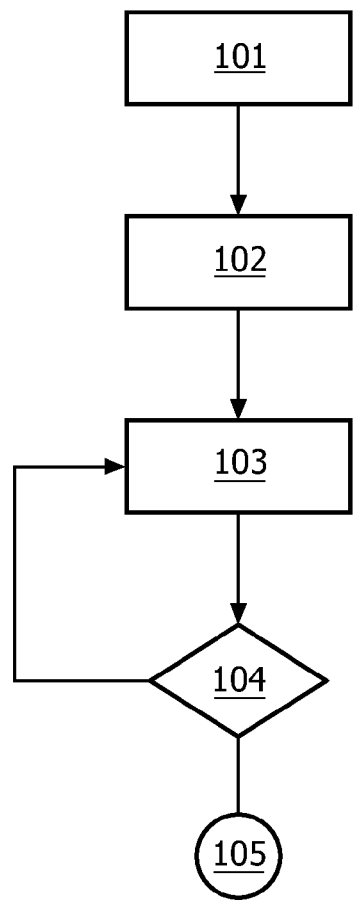
FIG. 8 shows a flow chart exemplarily illustrating an embodiment of a method for applying energy to an object and sensing the object.

In the following a method for applying energy to an object and sensing the object will be explained with reference to a flow chart shown in FIG. 8.

In step 101, the arrangement 7 is in the folded condition and located within the catheter 6 and the catheter 6 is guided to a desired location within the object by using the guiding control unit 23.

In step 102, by using the guiding control unit 23 the arrangement 7 leaves the catheter 6 and is transformed into the unfolded condition, which is shown in FIG. 3. The unfolded arrangement 7, which has now a basket structure, is guided such that it is in contact with the locations of the object 2, to which energy should be applied. Since the arrangement 7 comprises several optical fibers 14, which can apply light energy, and since each optical fiber 14 comprises a conductive coating 15 for electrically sensing the object, a multi-point energy application and sensing can be performed.

In step 103, the optical device 8 applies light energy via the optical fibers 14 at a plurality of locations and simultaneously the object is electrically sensed at these different locations, in order to monitor the application of light energy.

The application of the light energy and the monitoring is controlled by the second control unit 26 and, if the second control unit 26 detects that the sensed properties of the object are outside a predefined range, the second control unit 26 decides in step 104 that the application of the energy has to be stopped in step 105. It is further preferred that, if the second control unit 26 detects that an optical fiber is not in contact with the object, the application of the energy at least via this optical fiber is stopped.

Also if a user inputs into the second control unit 26, that the application of energy has to be stopped, the guiding control unit 23 stops the application of energy.

The guiding of the catheter 6 with the arrangement 7 within the object 2 is monitored by the imaging device 12.

Figure 9:
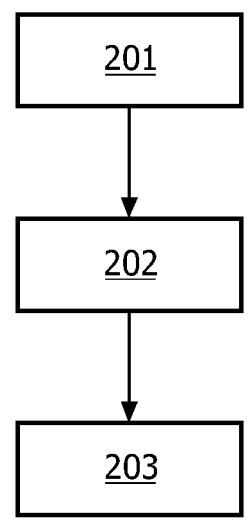
FIG. 9 shows a flow chart exemplarily illustrating an embodiment of a method for producing an apparatus for applying energy to an object and/or sensing the object.

In the following a method for producing an apparatus for applying energy to an object and sensing the object will be exemplarily explained with reference to a flow chart shown in FIG. 9.

In step 201, an optical device 8 for applying and/or sensing light energy, an electrical device 13 for applying and/or sensing electrical energy and at least one optical fiber 14 for applying light energy to the object and/or sensing the object is provided.

In step 202 on the at least one optical fiber 14 a conductive coating 15 is provided for forming at least one electrical conductor for applying electrical energy to the object and/or sensing the object. In this embodiment, in addition, the conductive coating 15 is coated with an electrically insulating coating 16.

In step 203 the at least one optical fiber 14 is connected with the optical device 8 and the at least one electrical conductor is connected with the electrical device 13.

In the above described embodiment, light energy is applied to the object and the object is electrically sensed. In another embodiment, electrical energy can be applied to the object using the electrical device and the electrical conductors formed by the conductive coating of the optical fibers and the object can be optically sensed using the optical device and the optical fibers. In this case, the electrical device is preferentially a plurality of electrical energy sources and the optical device is preferentially a spectroscope.

The apparatus 1 for applying energy to an object can be used, for example, for circumferential ablation and/or segmental ablation and/or a single point ablation.

While the invention has been illustrated and described in detail in the drawings and foregoing description such illustration and description are to be considered illustrative or exemplarily and not restrictive. The invention is not limited to the disclosed embodiments.

Other variations to the disclosed embodiments can be understood and effected by those skilled in the art and practicing the claimed invention, from a study of the drawings, the disclosure, and the appended claims.

In the claims the word "comprising" does not exclude other elements or steps and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the internet or other wired or wireless telecommunication systems.

Any reference signs in the claims should not be construed as limiting the scope of the invention.

The invention claimed is:

1. An apparatus for applying energy to an object and/or sensing the object wherein the apparatus comprises:
    an optical device;
    an electrical device;
    one or more optical fibers, each fiber including
        a single fiber core configured to connect to the optical device for applying light energy to the object and/or sensing the object, and
        a conductive coating configured to connect to the electrical device for applying electrical energy to the object and/or sensing the object, wherein the fiber core and the conductive coating are individually addressable;
    a casing in which the one or more optical fibers are located, wherein the casing comprises a window which is at least partly optically transparent for applying the light energy to the object and/or sensing the light energy from the object and at least partly electrically conductive for applying the electrical energy to the object and/or sensing the electrical energy from the object.

2. The apparatus as defined in claim 1, wherein the one or more optical fibers comprises a plurality of optical fibers.

3. The apparatus as defined in claim 2, wherein the window extends across at least two of the plurality of optical fibers for applying the light energy to the object and/or sensing the light energy from the object and for applying the electrical energy to the object and/or sensing the electrical energy from the object from the at least two of the plurality of optical fibers.

4. The apparatus as defined in claim 3, wherein the at least two of the plurality of optical fibers are coiled inside the casing such that the at least two of the plurality of optical fibers extend diagonally across the window.

5. The apparatus as defined in claim 1, wherein the conductive coating is coated with an electrically insulating coating.

6. The apparatus as defined in claim 1, wherein the one or more optical fibers comprise a plurality of optical fibers, and further comprising a combination element having a holding element, wherein the plurality of optical fibers are wound around the holding element.

7. The apparatus as defined in claim 1, wherein at least a part of the conductive coating is removed at a location, at which the window is optically transparent.

8. The apparatus as defined in claim 1, wherein the window comprises an optically transparent part and an electrically conductive part, and wherein the optically transparent part is not electrically conductive.

9. The apparatus as defined in claim 1, wherein at least a part of the window is formed by a tube-shaped or ring-shaped material arranged around the casing and a position, at which an opening is located in the casing.

10. The apparatus as defined in claim 1, wherein the window comprises alternately optically transparent and electrically conductive parts.

11. A method for applying energy to an object and/or sensing the object, wherein the method comprises acts of:
    providing one or more optical fibers each having a single fiber core and a conductive coating, wherein the fiber core and the conductive coating are individually addressable;
    connecting the fiber core to an optical device and the conductive coating to an electrical device;
    providing a casing including the one or more optical fibers and a window which is at least partly optically transparent and at least partly electrically conductive;
    applying light energy to the object and/or sensing light energy from the object through the window using the optical device; and
    applying electrical energy to the object and/or sensing electrical energy from the object through the window using the conductive coating.

12. The method as defined in claim 11, wherein the one or more optical fibers comprise a plurality of optical fibers, and further comprising an act of providing a combination element having a holding element, wherein the plurality of optical fibers are wound around the holding element.

13. The method as defined in claim 11, wherein at least a part of the conductive coating is removed at a location at which the window is optically transparent.

14. The method as defined in claim 11, wherein the one or more optical fibers comprise a plurality of optical fibers and the window extends across at least two of the plurality of optical fibers for applying the light energy to the object and/or sensing the light energy from the object and for applying the electrical energy to the object and/or sensing the electrical energy from the object from the at least two of the plurality of optical fibers.

15. The method as defined in claim 14, wherein the at least two of the plurality of optical fibers are coiled inside the casing such that the at least two of the plurality of optical fibers extend diagonally across the window.

16. A method for producing an apparatus for applying energy to an object and/or sensing the object, the method comprising acts of:
provided an optical device for applying and/or sensing light energy;
providing an electrical device for applying and/or sensing electrical energy;
providing one or more optical fibers each having a single fiber core and a conductive coating for applying electrical energy to the object and/or sensing the object, wherein the fiber core and the conductive coating are individually addressable;
connecting the fiber core with the optical device;
connecting the conductive coating with the electrical device; and
providing a casing in which the one or more optical fibers are located, wherein the casing comprises a window which is at least partly optically transparent for apply the light energy to the object and/or sensing the light energy from the object and at least partly electrically conductive for the applying the electrical energy to the object and/or sensing the electrical energy from the object.

17. The method as defined in claim 16, comprising an act of removing at least a part of the conductive coating at a location at which the window is optically transparent.

18. A computer program for applying energy to an object and/or sensing the object, when executed by a computer the computer program causing the computer to carry out a method for applying energy to an object and/or sensing the object using one or more optical fibers each including a single fiber core and a conductive coating, the method comprising acts of:
applying light energy to the object and/or sensing the light energy from the object through a window in a casing using an optical device connected to the fiber core of the one or more optical fibers, the fiber core and the conductive coating are being individually addressable, the casing surrounding the one or more optical fibers; and
applying electrical energy to the object and/or sensing the electrical energy from the object through the window using an electrical device connected to the conductive coating of one or more optical fibers.

19. The computer program as defined in claim 18, wherein at least a part of the conductive coating is removed at a location at which the window is optically transparent.

* * * * *